United States Patent [19]

Afonso et al.

[11] Patent Number: 5,190,956

[45] Date of Patent: Mar. 2, 1993

[54] CERTAIN N-SUBSTITUTED 3-OXIMINO-2,4-DIOXOQUINOLIN-2,4-(1H)DIONES USEFUL FOR TREATING VIRAL INFECTIONS

[75] Inventors: Adriano Afonso, West Caldwell; Jay Weinstein, Upper Montclair; Margaret J. Gentles, Bloomfield, all of N.J.

[73] Assignee: Schering Corporation, Kenilworth, N.J.

[21] Appl. No.: 579,919

[22] Filed: Sep. 7, 1990

[51] Int. Cl.$^5$ .................. C07D 215/20; C07D 215/22; A61K 31/47

[52] U.S. Cl. .................................. 514/312; 546/155; 549/400; 549/23; 564/265; 514/432; 514/456; 514/640

[58] Field of Search .............. 549/400; 514/456, 312; 546/155

[56] References Cited

U.S. PATENT DOCUMENTS

| | | | |
|---|---|---|---|
| 3,132,140 | 5/1964 | Jaffe | 546/7 |
| 4,022,770 | 5/1977 | L'Eplattenier et al. | 546/7 |
| 4,959,363 | 9/1990 | Wentland | 514/235.2 |

FOREIGN PATENT DOCUMENTS

| | | | |
|---|---|---|---|
| 93521 | 11/1983 | European Pat. Off. | 546/157 |
| 6916373 | 7/1969 | Japan | 546/155 |
| 2-152966 | 6/1990 | Japan | 546/155 |

OTHER PUBLICATIONS

Chemical Abstracts vol. 76(5), Abst. 24862-C. Jan. 31, 1972.
Derwent Abstract J90005-752-B.
Derwent Abstract J89035-827-B.
J. Chem. Soc. 438 (1964).
CA: 97:15948t (1982).
CA: 104124s (1981).

*Primary Examiner*—Alan L. Rotman
*Attorney, Agent, or Firm*—Eric S. Dicker; Henry C. Jeanette; Matthew Boxer

[57] ABSTRACT

Compounds useful as antiviral agents against DNA containing viruses, such as herpes group viruses, are disclosed. The compounds are selected from the group consisting of:

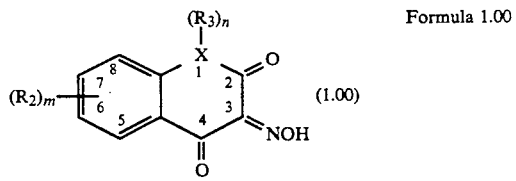

and their pharmaceutically acceptable salts and solvates.

Pharmaceutical compositions containing compounds represented by Formula 1.00 are disclosed. Also disclosed are methods of treating a viral infection using compounds represented by Formula 1.00.

The compounds of Formula 1.00 are also useful as intermediates to compounds of:

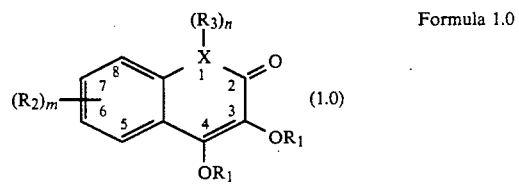

Compounds of Formula 1.0 are useful as antiviral agents against the same viruses that the compounds of Formula 1.00 are useful against.

6 Claims, No Drawings

CERTAIN N-SUBSTITUTED 3-OXIMINO-2,4-DIOXOQUINOLIN-2,4-(1H)DIONES USEFUL FOR TREATING VIRAL INFECTIONS

REFERENCE TO RELATED APPLICATIONS

This application is related to application Ser. No. 07/579,125 filed Sep. 7, 1990, now abandoned.

BACKGROUND

This invention relates to compounds having antiviral activity, pharmaceutical compositions thereof, and methods of treatment utilizing the compositions. In particular, this invention is related to compounds having antiviral activity against herpes group viruses, pharmaceutical compositions containing the compounds, and methods of treating herpes group viruses using the pharmaceutical compositions.

There are four seperate herpes group viruses which infect and cause disease in humans. These are (1) herpes simplex virus 1 and 2 (HSV-1 and HSV-2, respectively); (2) cytomegalovirus (CMV); (3) varicella-zoster virus (VZ); and (4) Epstein-Barr virus (EB). Examples of diseases associated with herpes simplex virus infection include herpes labialis, genital herpes(herpes progenitalis), neonatal herpes, herpetic keratitis, eczema herpecticum, disseminated herpes, occupational herpes, herpectic gingivostomatitis, meningitis (aseptic), and encephalitis.

VZ virus is associated with chicken-pox (varicella) and shingles (zoster) in humans.

CMV is wide spread in humans and numerous other mammals. A great majority of humans CMV infections are subclinical; that is, the primary infection occurs with no signs or symptoms. An exception to this is a congenital infection which occassionally gives rise to cytomegalic inclusion body disease in infants. There is also a mononucleosis-like syndrome caused by the virus.

A great majority of serious cases due to CMV infection come from recurring infections in immuno-compromised individuals, such as in transplant patients and in cancer patients. It has been estimated that silent CMV infections have occurred in a majority of humans by the time adulthood is reached.

Examples of drugs used to treat herpes infections include: (1) IUDR (5'-iodo-2'-deoxyuridine); (2) Ara-C (1-[beta-D-arabinofuranosyl]-cytosine); (3) Ara-A (9-beta-D-arabinofuranosyladenine); and (4) Acyclovir (9-[(2-hydroxyethoxy)methyl]guanine). Also Haines et al. (U.S. Pat. No. 4,757,088 issued Jul. 12, 1988) discloses that lidocaine (2-(diethylamino)-N-(2,6-dimethylphenyl)acetamide) is an antiviral agent in cell culture against HSV-1 and HSV-2, and is able to treat herpes virus infections of mammals. Haines et al. also disclose that lidocaine is particularly effective in the treatment of HSV oral and genital lesions in humans. According to Haines et al., the addition of pantothenic acid or its alcohol and salt forms, dexpanthenol and pantothenate respectively, to lidocaine or lidocaine hydrochloride significantly enhances the antiviral activity of those drugs.

In view of current interest in the art for finding useful antiviral agents, in particular, useful agents against herpes group viruses, any new compounds exhibiting antiviral activity and/or useful for making compounds exhibiting antiviral activity would be a welcome contribution to the art. This invention provides such a contribution.

SUMMARY OF THE INVENTION

This invention provides compounds which are intermeiates to antiviral compounds and which are themselves useful, as are the antiviral compounds produced from the intermediates, as antiviral agents against DNA containing viruses such as herpes group viruses. In particular, the compounds of this invention are useful against HSV-1 and HSV-2 and may also prove useful against CMV and EB.

The compounds of this invention are advantageous over known compounds because they inhibit early events in the viral replication.

One embodiment of this invention provides compounds of:

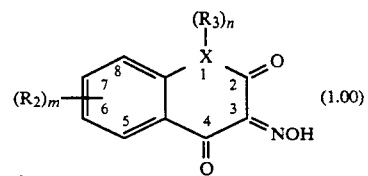

Formula 1.00

(1.00)

wherein:
(A) X is selected from the group consisting of N, O, S, and C;
(B) m is an integer from 0 to 4;
(C) Each $R_2$ for each m is independently selected from the group consisting of:
(1) alkyl;
(2) alkoxy;
(3) aryloxy;
(4) aryl;
(5) aralkyloxy;
(6) halogen atoms selected from the group consisting of: F, Cl, Br and I;
(7)

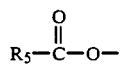

wherein $R_5$ is selected from the group consisting of: alkyl, alkaryl, alkenyl, heteroalkyl, and heteroaryl;

(8)

wherein each $R_6$ is independently selected from the group consisting of: H, alkyl, aryl and $R_5C(O)$— wherein $R_5$ is as above defined;

(9)

(10)

(11)

(12)

wherein $R_7$ is selected from the group consisting of: alkyl and aryl;

(13)

(14)

wherein $R_8$ is selected from the group consisting of: alkyl, aryl and H;

(15)

and (16)

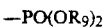

wherein $R_9$ is selected from the group consisting of: alkyl and aryl;

(17) —$OPO_3H$;
(18) —$OP(OR_9)_2$ wherein $R_9$ is as above defined; and
(19) —$CF_3$;

(D) n is:
(1) 1 when X is N;
(2) 0 when X is S;
(3) 0 when X is O; and
(4) 2 when X is C, and each $R_3$ is the same or different;

(E) $R_3$ is selected from the group consisting of:
(1) alkyl;
(2) aralkyl;
(3) aryl;
(4) substituted aryl;
(5) alkaryl;
(6) alkyl heteroaryl;
(7) alkyloxyalkyloxyaryl;
(8) —$(CH_2)_a R_{10}$ wherein a is an integer of 1 to 6 and $R_{10}$ is selected from the group consisting of:
   (a) —$C(O)OR_{11}$ is selected from the group consisting of alkyl, alkenyl, and H;
   (b) —$N(R_{11})_2$ wherein each $R_{11}$ is the same or different, and $R_{11}$ is as defined above;
   (c) —$R_{11}$ wherein $R_{11}$ is as defined above;
   (d) —$OR_{11}$ wherein $R_{11}$ is as defined above;
(9) H; and
(10) —$OR_{12}$ wherein $R_{12}$ is selected from the group consisting of H, alkyl, alkaryl, alkenyl, heteroaryl, and heteroalky.

Those skilled in the art with appreciate that compounds of Formula 1.00 can also exist in the tautomeric form represented by Formula 1.0:

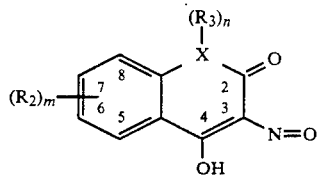

(1.01)

and that reference herein to Formula 1.00 includes reference to Formula 1.01.

Another embodiment of this invention provides pharmaceutical compositions comprising an effective amount of a pharmaceutically acceptable carrier and an effective amount of a compound of this invention. Preferably the compound is selected from the group of compounds represented by Formulas 1.02 to 1.07 defined below. The pharmaceutical compositions are useful in treating viral infections in a patient in need of such treatment.

In yet another embodiment this invention provides a method of treating a patient having a viral infection by administering to such a patient an effective amount of a compound of this invention. Generally, the compound is administered as one of the pharmaceutical compositions of this invention. Examples of viral infections treatable in accordance with the methods of this invention include the DNA containing viruses such as the herpes viruses discussed above (e.g., HSV-1, HSV-2, CMV, VZ, EB, and the like).

The compounds of Formula 1.00 are useful as intermediates to the compounds of Formula 1.0:

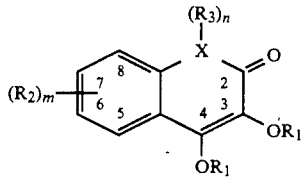

(1.0)

wherein:
(A) X, m, $R_2$, $R_3$ and n are as defined above; and
(B) $R_1$ is selected from the group consisting of:
(1) alkyl;
(2) aryl;
(3) acyl of the formula —$C(O)R_4$ wherein $R_4$ is selected from the group consisting of: H, aryl, alkaryl, alkenyl, —$NH_2$, —$NHR_5$, —$N(R_5)_2$, heteroalkyl, heteroaryl, and substituted alkyl wherein $R_5$ is selected from the group consisting of: alkyl, alkaryl, alkenyl, heteroalkyl, and heteroaryl;
(4) heteroaryl; and
(5) H.

Compounds of Formula 1.0 are useful in treating the same viral infections disclosed as being treatable by the compounds of Formula 1.00.

DETAILED DESCRIPTION OF THE INVENTION

When used herein, the terms listed below have the scope indicated, unless indicated otherwise.

Alkaryl—represents an aryl group, as defined below, in which an alkyl group, as defined below, is substituted for one of the aryl H atoms. The aryl group may contain additional substituents selected from the group consisting of: halogen atoms (e.g, Cl, Br, F, and/or I), alkoxy, alkyl, and amino. Representative examples include: $CH_3$phenyl-, $CH_3CH_2$phenyl- and the like.

Alkenyl (alkylene)—represents straight and branched carbon chains having at least one carbon to carbon double bond and preferably having from 2 to 6 carbon atoms. Preferably the alkenyl substituent has from 1 to 2 double bonds. Representative examples include vinyl, allyl, butenyl and the like.

Alkoxy—represents an alkyl radical attached to a molecule through an oxygen atom (—O-alkyl). Representative examples include methoxy, ethoxy and the like.

Alkynyl—represents a straight or branched hydrocarbon chain having at least one carbon-to-carbon triple bond, and having from 3 to 8 carbon atoms with from 3 to 6 carbon atoms being preferred. Representative examples include propynyl, butynyl and the like.

Alkyl—represents straight or branched carbon chains, which contain from 1 to 6 carbon atoms. Representative examples include methyl, ethyl, propyl and the like.

Alkyl heteroaryl(alkheteroaryl)—represents a heteroaryl group, as defined below, wherein an alkyl group, as defined above, is substituted for one of the aryl H atoms. Representative examples include pyridylmethyl, furylmethyl and the like.

Alkyloxyalkyloxyaryl—represents a group wherein an alkyl group is joined through an oxygen atom to another alkyl group which in turn is joined through an oxygen atom to an aryl group wherein the point of attachment to the aryl group is at a ring carbon. Alkyl is as defined above and aryl is as defined below. The aryl group may contain additional substituents selected from the group consisting of: halogen atoms (e.g., Cl, Br, F, and/or I), alkoxy, alkyl, and amino. Representative examples include phenoxypropyloxymethyl, phenoxyethoxymethyl and the like.

Aralkyl—represents an alkyl group as defined above in which an aryl group as defined below is substituted for one of the alkyl hydrogen atoms. Representative examples include —$CH_2$phenyl, —$CH_2CH_2$phenyl, 4-hydroxybenzyl, 4-t-butyldimethylsilyloxybenzyl, and the like.

Aralkyloxy—represents an aralkyl group as defined above, which is attached to a molecule by an oxygen atom (aralkyl-O—). The aryl group may contain additional substitutents selected from the group consisting of: halogen atoms (e.g., Cl, Br, F, and/or I), alkoxy, alkyl, and amino. Representative examples include benzyloxy, phenethoxy, and the like.

Aryl—represents a mono or bi-cyclic aromatic system. Examples of preferred aryl groups include those having from 6 to 14 carbon atoms. Representative examples include phenyl, 1-naphthyl, 2-naphthyl and indanyl. The aryl group may contain additional substituents selected from the group consisting of: halogen atoms (e.g., Cl, Br, F, and/or I), alkoxy, alkyl, and amino.

Aryloxy—represents an aryl group as defined above, which is attached through an oxygen atom (aryl-O—). The aryl may contain additional substituents selected from the group consisting of: halogen atoms (e.g., Cl, Br, F, and/or I), alkoxy, alkyl, and amino. Representative examples include phenoxy, naphthyloxy, and the like.

Heteroalkyl—represents an alkyl group, as defined above, wherein one or more heteroatoms are substituted for one or more of the alkyl H atoms. The heteroatoms are independently selected from the group consisting of: O, S, and N. Representative examples of heteroalkyl groups include hydroxyethyl, aminoethyl, mercaptoethyl, and the like.

Heteroaryl (including the heteroaryl portion of heteroarylmethyl)—represents aromatic systems having at least one O, S and/or N heteroatom in the ring structure. Examples of preferred heteroaryl groups include those containing from 3 to 14 carbon atoms. Representative examples of heteroaryl groups include but are not limited to: 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, 2-or 3-pyrrolyl, 2- or 3-N-methylpyrrolyl, and the like.

Substituted alkyl—represents an alkyl group, as defined above, wherein one or more of the alkyl H atoms are replaced with groups selected from the group consisting of: alkyl, aryl, heteroaryl, —OH, —O-alkyl, —$NH_2$, —N(alkyl)$_2$ wherein each alkyl group is the same or different, —S-alkyl, —C(O)O-alkyl, —C(O)H, —NHC(NH)$NH_2$ (wherein the C(NH) portion represents C=NH), —C(O)$NH_2$, —OC(O)$NH_2$, $NO_2$ and —NHC(O)-alkyl, wherein alkyl, aryl, and heteroaryl are as above defined.

Substituted aryl—represents an aryl group, as defined above, wherein one of more of the H atoms attached to the ring carbon atoms are replaced by groups independently selected from the group consisting of: halo, alkyl, hydroxy, alkoxy, phenoxy, amino, alkylamino, and dialkylamino. Preferred substituted aryl groups are substituted phenyl groups.

Also, as used herein, unless indicated otherwise, C(O) represents C=O $R_1$ is preferably selected from the group consisting of: alkyl, acyl, and H. When $R_1$ is acyl, i.e., —C(O)$R_4$, $R_4$ is preferably selected from the group consisting of: alkyl, aryl, and heteroaryl (including substituted heteroaryl). Most preferably $R_4$ is selected from the group consisting of: methyl, ethyl, phenyl, 2-pyrrolyl, N-methyl-2-pyrrolyl, 5-bromo-2-furanyl, 4-pyridyl(4-pyridinyl), and 2-thiophenyl (2-thienyl).

Representative examples of $R_1$ include, but are not limited to:

(1) H;
(2) methyl;
(3) pyrrol-2-ylcarbonyl (pyrrol-2-carbonyl)

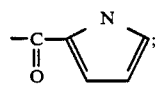

(4) N-methylpyrrol-2-ylcarbonyl(N-methylpyrrol-2-carbonyl)

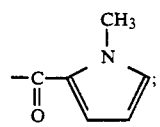

(5) 2-thiophenecarbonyl (2-thienylcarbonyl)

(6) 5-bromo-furanylcarbonyl $-\underset{\underset{O}{\|}}{C}-\underset{Br}{\underset{O}{\bigcirc}}$ ;

(7) isonicotinoyl $-\underset{\underset{O}{\|}}{C}-\underset{N}{\bigcirc}$ ;

(8) benzoyl $-\underset{\underset{O}{\|}}{C}-\bigcirc$ ;

(9) acetyl $-\underset{\underset{O}{\|}}{C}-CH_3$ ;

(10) propionyl $-\underset{\underset{O}{\|}}{C}-CH_2CH_3$ ;

(11) and the like.

Examples of $R_2$ include, but are not limited to:

(1)

—$CH_3$;

(2)

—$OCH_3$;

(3)

$CH_3\underset{\underset{O}{\|}}{C}-O-$ ;

(4)

$\bigcirc-CH_2O-$ ;

(5) Cl;
(6) F and;
(7) I; and
(8) —$CF_3$.

Examples of $R_3$ include, but are not limited to:

(1)

—$CH_3$;

(2)

—$C_6H_{13}$;

(3)

—$C_7H_5$ (4)

$\bigcirc-CH_2-$ ;

(5)

$-CH_2-\bigcirc-O-\underset{\underset{CH_3CH_3}{|}}{\overset{\overset{CH_3CH_3}{|}}{Si}}-\underset{\underset{CH_3CH_3}{|}}{\overset{\overset{}{|}}{C}}-CH_3$ ;

(6)

$\bigcirc$ ;

(7)

$-CH_2OCH_2CH_2CH_2O-\underset{Cl}{\bigcirc}-OCH_3$ ;

(8)

$-CH_2\underset{\underset{O}{\|}}{C}OCH_2CH=CH_2$ ;

and (9)

$-CH_2\underset{\underset{O}{\|}}{C}OCH_3$ .

Preferably $R_3$ is selected from the group consisting of: methyl, heptyl, phenyl and benzyl.

Preferably X is nitrogen.

Examples of compounds of Formula 1.00 include, but are not limited to, compounds of Formulas:

(A) Formula 1.02

$\underset{}{\bigcirc}\underset{\underset{O}{\|}}{\overset{\overset{CH_3}{|}}{N}}\underset{\underset{\underset{O}{\|}}{NOH}}{\overset{\overset{O}{\|}}{}}$ (1.02);

-continued
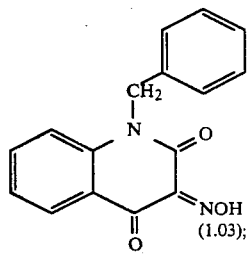
(B) Formula 1.03
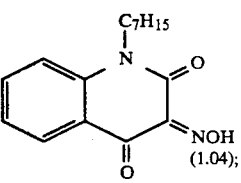
(C) Formula 1.04
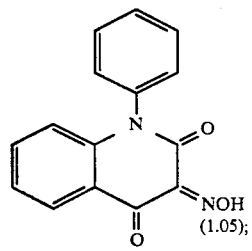
(D) Formula 1.05
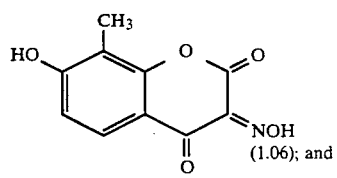
(E) Formula 1.06
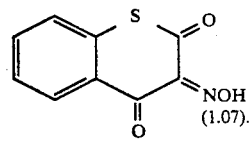
(F) Formula 1.07
Compounds of this invention are used to make compounds of Formula 1.0. Examples of compounds of Formula 1.0 include, but are not limited to:
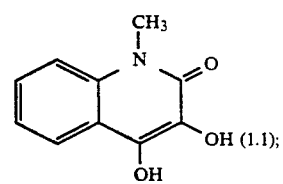
(A) Formula 1.1
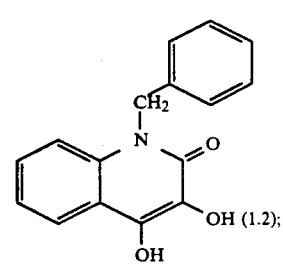
(B) Formula 1.2
-continued
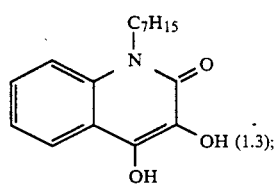
(C) Formula 1.3
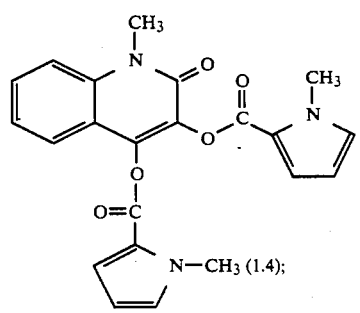
(D) Formula 1.4
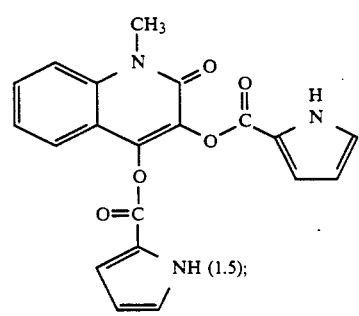
(E) Formula 1.5
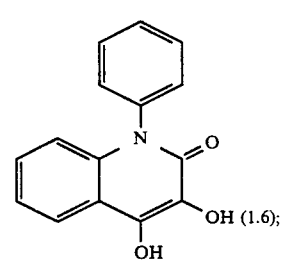
(F) Formula 1.6
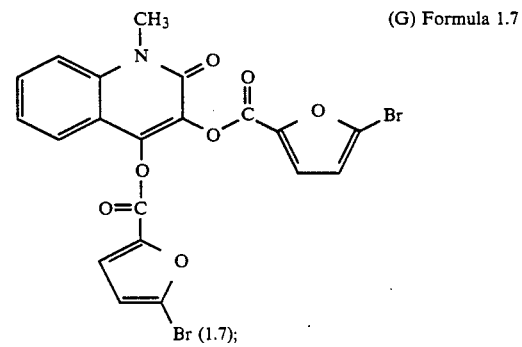
(G) Formula 1.7

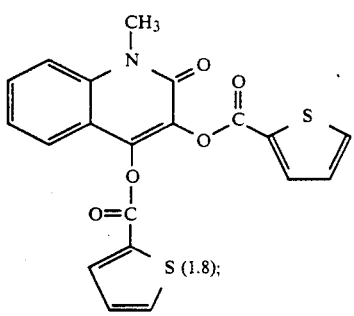 (H) Formula 1.8

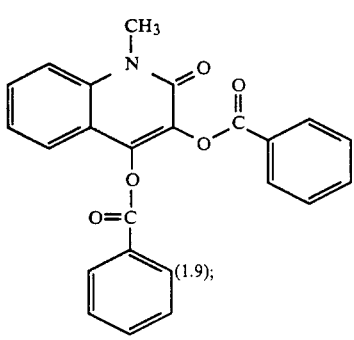 (I) Formula 1.9

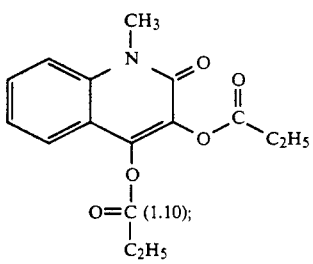 (J) Formula 1.10

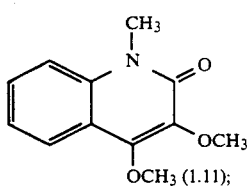 (K) Formula 1.11

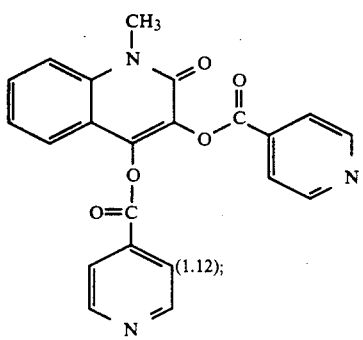 (L) Formula 1.12

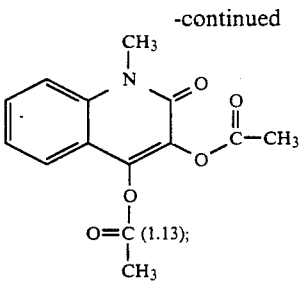 (M) Formula 1.13

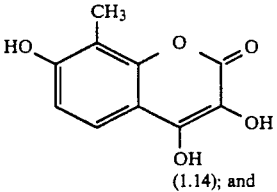 (N) Formula 1.14

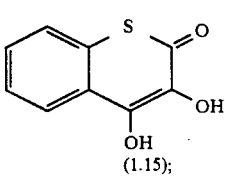 (O) Formula 1.15

Preferred compounds of this invention are selected from the group consisting of: Formulas 1.02, 1.03, and 1.04.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general such as water, ethanol and the like are equivalent to the unsolvated forms for purposes of the invention.

Certain compounds of the invention will be acidic in nature, e.g., those compounds which possess a carboxyl or phenolic hydroxyl group. These compounds may form pharmaceutically acceptable salts. Examples of such salts are the sodium, potassium, calcium, and aluminum. salts. Also contemplated are salts formed with pharmaceutically acceptable amines such as ammonia, alkylamines, hydroxyalkylamines, N-methylglucamine and the like.

Certain compounds of the invention, e.g., those with a basic amine group, also form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the are. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of this invention.

The compounds of Formula 1.0 can be prepared by the processes described below. In these processes the substituents are as described above, unless indicated otherwise. Those skilled in the art will appreciate that the processes described below the reactions are carried out at a temperature high enough to allow the reaction to proceed at a reasonable rate, but not so high as to cause undue degradation of reactants and/or products. Those skilled in the art will also appreciate that in the following reactions the desired products may be isolated by techniques well known in the art such as distillation, column chromatography, recrystallization, and the like.

The compounds of Formula 1.00 can be prepared in accordance with the reactions set forth in Scheme I. The abbreviation "EQ" as used hereinafter stands for Equation.

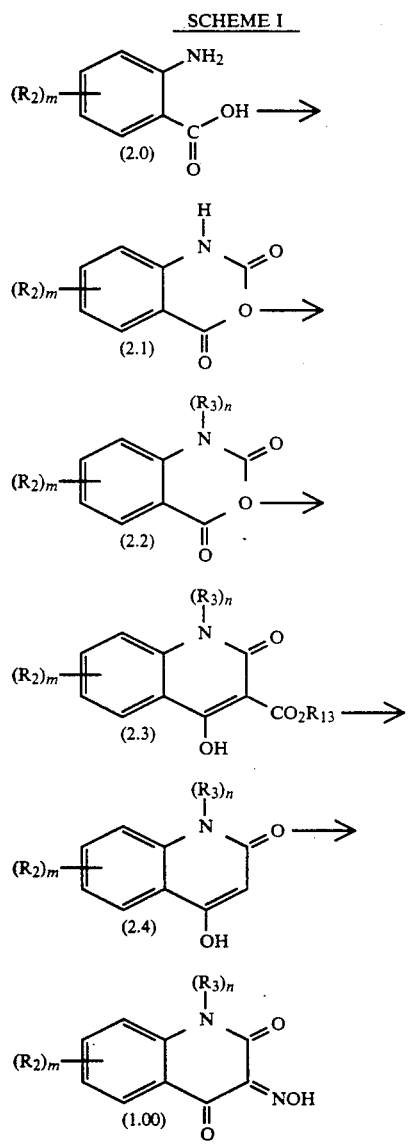

EQ 1.0, 1.1, and 1.2 represent reactions well known to those skilled in the art, see, for example: G. M. Coppola, et al., *Synthesis*, 505 (1980); the disclosure of which is incorporated herein by reference thereto.

In EQ 1.0 a suitable 2-aminobenzoic acid (2.0) in a water and 2N Hcl solution is reacted with trichloromethyl chloroformate to form an isatoic anhydride (2.1). The aminobenzoic acid (2.0) used will have the appropriate $R_2$ substitutent group to give the desired ultimate end product. $R_2$ and m are as defined above.

In EQ 1.1, the isatoic anhydride (2.1) is reacted with a suitable halide of $R_3$ (wherein $R_3$ and n are as above defined) to produce the desired substituted isatoic anhydride (2.2).

In EQ 1.2, the isatoic anhydride is reacted with the anion derived from a malonate ester to produce the quinolone(2.3). $R_{13}$ is ethyl when ehtyl malonate is used.

In EQ 1.3, the quinolinone (2.3) is decarboxylated to produce the quinolinone (2.4). Generally this reaction is carried out by procedures well known in the art—see, for example, G. M. Coppola et al., *J. Org. Chem.*, 41, 825 (1976), the disclosure of which is incorporated herein by reference thereto.

In EQ 1.4, the compound of Formula (2.4) is converted to the compound of Formula (1.00) by following standard reaction conditions for nitrosation, see, for example, J. March, *Adv. Org. Chem.*, John Wiley & Sons Publishers, 1985, p. 535, the disclosure of which is incorporated herein by reference thereto.

The compounds of Formula 1.00 can then be converted to compounds of Formula 1.0 in accordance with Equations 1.5 and 1.6.

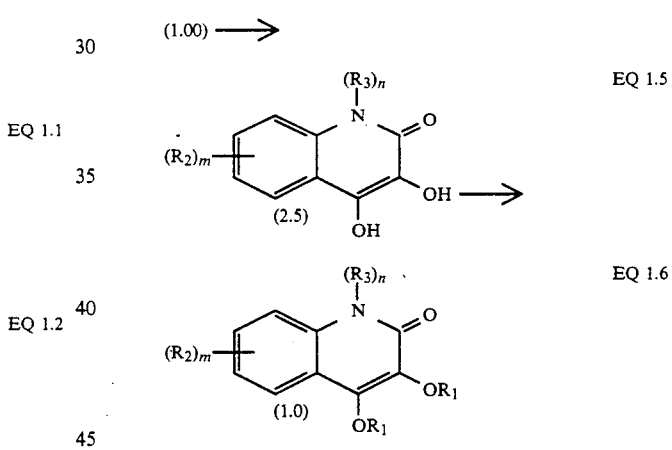

In EQ 1.5, the compound of Formula 1.00 is reductively hydrolyzed to produce a compound of Formula 2.5. The reaction is carried out by stirring a mixture of a compound of Formula 1.00 and a hydrogenation catalyst in an acidic solvent mixture under hydrogen.

The hydrogenation catalyst used in EQ 1.5 may be of the palladium, platinum or nickel type; preferably the catalyst is 5-20% palladium on carboxy; most preferably the catalyst is 10% palladium on carbon. The amount of catalyst used is from about 0.01 to about 0.5 parts by weight based on the weight of the compound (substrate) of Formula 1.00; preferably about 0.1 to about 0.5 parts by weight and most preferably about 0.3 parts by weight of catalyst is used.

The acidic solvent used in the reaction of EQ 1.5 comprises a mixture of an organic solvent, such as an alcohol (e.g., ethanol, methanol, propanol, isopropanol, and the like), glacial acetic acid, tetrahydrofuran, dimethylformamide and the like, containing a mineral acid such as hydrochloric or sulfuric acid. Preferably the solvent is ethanol or glacial acetic acid containing aqueous hydrochloric or sulfuric acid; most preferably the solvent comprises a mixture of 100 parts of ethanol and 50 parts of 2N-hydrochloric acid for 1 part of substrate (compound) of Formula 1.00 (Vol/Wt).

The hydrogenation in EQ 1.5 is carried out at pressures ranging from atmospheric pressure to several p.s.i.; preferably the reaction is carried out at atmospheric pressure to 15 p.s.i. and most preferably at atmospheric pressure. The reaction is complete when no further uptake of hydrogen is observed.

In EQ 1.6, the compound of Formula (2.5) is reacted with an appropriate halide of $R_1$ in order to produce the desired ether, or with an appropriate acyl halide to produce an ester at C-3 and C-4. The reactions are carried out by procedures well known in the art; for example, see J. March, *Adv. Org. Chem.*, cited above, Section 0.14, p. 342, for producing the ethers, and see J. March, *Adv. Org. Chem.*, cited above, Section 0.22, p. 346, for producing the esters, the disclosures of each being incorporated herein by reference thereto.

The compounds of this invention can be administered in any number of conventional dosage forms, e.g., topical, oral, parenteral, rectal, transdermal, inhalation and the like. Oral or rectal dosage forms include capsules, tablets, pills, poweders, cachets and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conventiently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration, by employing an antiviral effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide antiviral activity. For example, when administered orally doses of from about 20 to about 60 mg/kg of body weight may be used; and when administered parenterally, e.g., intravenously, dosages of from about 5 to about 20 mg/kg body weight may be used.

When administered topically, the amount of compound administered varies widely with the amount of skin being treated, as well as with the concentration of active ingredient applied to the affected area. Preferrably, topical compositions contain from about 0.10 to about 10 percent by weight of the active ingredient and are applied as needed according to the judgment of the attending clinician. When administered rectally, the compounds of this invention may be administered in daily doses ranging from about 0.1 mg/kg to about 100 mg/kg.

The dosage to be administered and the route of administration depends upon the particular compound used, the age and general health of the patient and the severity of the viral condition. Thus, the dose ultimately decided upon must be left to the judgment of a trained health-care practitioner.

EXAMPLES

The following examples are illustrative only and should not be construed as limiting the invention in any way. Those skilled in the art will appreciate that variations are possible which are within the spirit and scope of the appended claims.

In the examples, Ar represents aromatic.

PREPARATION A

1-Benzyl-4-Hydroxy-2(1H)-Quinolinone (1) A solution of isatoic anhydride (4.1 gm) in DMF (30 ml) was added dropwise to a stirred suspension of 60% sodium hydride (1.0 gm) in DMF (20 ml) under nitrogen atmosphere. The reaction mixture was then warmed to 45° C. and stirred until hydrogen evolution ceased. The reaction mixture was then cooled and a solution of benzyl bromide (4.4 gm) in DMF (10 ml) was added slowly. Stirring was continued for one hour at room temperature and the solution was then evaporated under reduced pressure at 45° C. The resulting solid was removed by filtration and the filtrate was evaporated to give 1-benzylisatoic anhydride.

(2) Diethyl malonate (4.07 gm) in dimethyl acetamide (DMA) (10 ml) was added dropwise to a stirred suspension of 60% sodium hydride (1.01 gm) in the same solvent (10 ml), under a nitrogen atmosphere, in an oil bath at 25° C. After hydrogen evolution ceased, the temperature was raised to 80° C. while adding a solution of 1-benzylisatoic anhydride (4.2 gm) in DMA (50 ml). After carbon dioxide evolution ceased, the reaction mixture was heated at 120° C. for 17 hours and then concentrated under reduced pressure to a volume of 25 ml, and then diluted with water (50 ml). The milky solution was washed with ether, the aqueous layer was acidified with mineral acid to pH3 and the resulting crystalline product 1-benzyl-3-carbethoxy-2(1H)-quinolinone was added to 2N sodium hydroxide (150 ml). The mixture was refluxed for 4 hrs and the resulting solution was then cooled, acidified with mineral acid to pH3 and the solid was filtered, dried and crystallized from ethyl acetate/hexane to give the title compound (4.0 gm). That the expected product was obtained was confirmed by the spectral data: MS: m/e 251 (M.+); NMR (DMSO): $\delta 5.47$ (s,2H,CH$_2$Ar), 6.03(s,1H,=CH), 11.6 (s,1H,OH) ppm.

PREPARATION B

1-Heptyl-4-Hydroxy-2(1H)-Quinolinone

Obtained by using heptyl bromide in Step (1) of Preparation A. That the expected product was obtained was confirmed by the spectral data: MS: m/e 259 (M.+); NMR (DMSO): $\delta 0.9$(t, 3H, CH$_3$—CH$_2$), 4.06 (t, 2H, N—CH$_2$), 6.18 (s, 1H, =CH), 11.87 (br, 1H, OH) ppm.

PREPARATION C

1-Phenyl-4-Hydroxy-1(1H)-Quinoline

Obtained by starting with N-phenyl-isatoic anhydride and using the procedure described in Step (2) of Preparation A. That the expected product was obtained was confirmed by the spectral data: MS: m/e 237 (M.+); NMR (DMSO): $\delta 5.92$ (s, 1H, =CH), 11.60 (s, 1H, OH) ppm.

EXAMPLE 1

1-Methyl-3-Oximino-Quinolin-2,4(1H)-Dione (Formula 1.02)

Glacial acetic acid (2.7 ml) was added with stirring to a solution of 1-methyl-4-hydroxy-2(1H)-quinolinone (1.75 gm, see G. M. Copploa, *J. Org. Chem.*, 41, 825, (1976), already cited above) and sodium nitrite (0.8 gm) in a solvent mixture consisting of methanol (17.5 ml), ethyl acetate (20 ml) and water (10 ml) under nitrogen atmosphere. The reaction mixture was stirred for 1.5 hrs at room temperature and the organic solvents were then removed under reduced pressure. The resulting suspension was filtered and the solid washed with water to give the title compound. That the expected product was obtained was confirmed by the spectral data: MS: m/e 204 (M.+); NMR (DMSO): $\delta 3.44$ (s, 3H, CH$_3$—N), 15.34 (br, 1H, =NOH) ppm.

EXAMPLE 2

1-Benzyl-3-Oximino-Quinoline-2,4(1H)-Dione (Formula 1.03)

Obtained by nitrosation of 1-benzyl-4-hydroxy-2(1H)-quinolinone (Preparation A) using the procedure described in Example 1. That the expected product was obtained was confirmed by the spectral data: MS: m/e 280 (M.+); NMR (DMSO): δ5.35(s, 2H, CH$_2$—Ar), 15.3 (br, 1H, =NOH) ppm.

EXAMPLE 3

1-Heptyl-3-Oximino-Quinolin-2,4(1H)-Dione (Formula 1.04)

Obtained by nitrosation of 1-heptyl-4-hydroxy-2(1H)-quinolinone (Preparation B) using the procedure described in Example 1. That the expected product was obtained was confirmed by the spectral data: MS: m/e 288 (M.+); NMR (DMSO): δ0.85 (t, 3H, CH$_3$—), 1.28 (br, 6H, —CH$_2$—), 1.62 (br, 2H, —CH$_2$—), 4.02(t, 2H, CH$_3$—N), 15.37(br,1H,=NOH) ppm.

EXAMPLE 4

1-Phenyl-3-Oximino-Quinolin-2,4(1H)-Dione (Formula 1.05)

Obtained by nitrosation of 1-phenyl-4-hydroxy-2(1H)-quinolinone (Preparation C) using the procedure described in Example 1. That the expected product was obtained was confirmed by the spectral data: MS: m/e 266 (M.+); NMR (DMSO): δ15.19 (br, 1H, =NOH) ppm.

EXAMPLE 5

3-Oximino-7-Hydroxy-8-Methyl-Benzopyran-2,4-Dione (Formula 1.06)

Obtained by nitrosation of 4,7-dihydroxy-8-methyl-coumarin (JACS, 80, 140, 1958, the disclosure of which is incorporated herein by reference thereto) using the procedure described in Example 1. That the expected product was obtained was comfirmed by the spectral data: MS: m/e 221 (M.+).

EXAMPLE 6

3-Oximino-4-Oxo-Dihydro-1,2-Benzothiopyrone (Formula 1.07)

If the following procedure were to be followed then the title compound would be obtained.

Step (1): Preparation of 4-Hydroxy-1,2-Benzothiopyrone.

A solution of thiosalicylic acid (3.0 g) in methanol (30 ml) is cooled in an ice bath and dry hydrogen chloride is bubbled in for 15 minutes. The solution is allowed to stand at room temperature for 24 hours and then evaporated. The resulting methyl thiosalicylate is dissolved in pyridine (20 ml) containing acetic anhydride (5 ml). After 24 hrs the reaction mixture is diluted with ethyl acetate, washed several times with water, dried and evaporated. The resulting acetylthiosalicylic acid methyl ester is dissolved in dimethylformamide (20 ml), cooled to 0° C. and 60% sodium hydride (0.8 g) is added while stirring. The reaction mixture is then stirred room temperature for 12 hours, concentrated to half volume under reduced pressure, diluted with water and acidified to pH3 with mineral acid and filtered to give the title compound.

Step (2): Preparation of 3-Oximino-4-oxo-dihydro-1,2-benzothiopyrone.

Is obtained by nitrosation of 4-hydroxy-1,2-benzothiopyrone (Step 1) using the procedure described in Example 1.

INTERMEDIATE TO FINAL PRODUCT

The compounds of the invention (Formula 1.00), as stated above, are intermediates to compounds of Formula 1.0 (defined above). The following examples illustrate the use of the compounds of Formula 1.00 to produce the compounds of Formula 1.0.

EXAMPLE 7

1-Methyl-3,4-Dihydroxy-2(1H)-Quinolinone; (Formula 1.1 from Formula 1.02)

A suspension of 1-methyl-3-oximino-quinolin-2,4(1H)-dione (1.7 gm, Formula 1.02, Example 1) and 10% palladium on charcoal (0.5 gm) in a mixture of ethanol (90 ml) and 2N hydrochloric acid (40 ml) was hydrogenated at atmospheric conditions. After 2.5 hrs no further uptake of hydrogen (510 ml) was observed. The reaction mixture was filtered and the solid cake was extracted with hot glacial acetic acid (2×100 ml). The combined filtrates were evaporated under reduced pressure and the produce was crystallized from acetic acid/water to give the title compound (1.6 gm). That the expected product was obtained was confirmed by the spectral data: MS (FAB): m/e 192 (M.+ +1); NMR (DMSO): δ3.66 (s, 3H, CH$_3$—N), 8.79 (s, 1H, OH), 10.16 (s, 1H, OH) ppm.

EXAMPLE 8

1-Benzyl-3,4-Dihydroxy-2(1H)-Quinolinone (Formula 1.2 from Formula 1.03)

Obtained from 1-benzyl-3-oximino-quinolin-2,4(1H)-dione (Formula 1.03, Example 2) using the hydrolytic reduction procedure described in Example 7. That the expected product was obtained was confirmed by the spectral data: MS: m/e 267 (M.+); NMR (DMSO): δ5.59 (s, 2H, CH$_2$—Ar), 8.92 (br, 1H, OH), 10.32 (br, 1H, OH) ppm.

EXAMPLE 9

1-Heptyl-3,4-Dihydroxy-2(1H)-Quinolinone (Formula 1.3 from Formula 1.04)

Obtained from 1-heptyl-3-oximino-quinolin-2,4(1H)-dione (Formula 1.04, Example 3) using the hydrolytic reduction procedure described in Example 7. That the expected product was obtained was confirmed by the spectral data: MS: m/e 275 (M.+); NMR (DMSO): δ0.84 (t, 3H, CH$_3$—), 1.28 (m, 8H,—CH$_2$—), 1.62 (m, 2H, —CH$_2$—), 4.27 (t, 2H, CH$_2$—N), 8.76 (d, 1H, OH), 10.16 (d, 1H, OH) ppm.

EXAMPLE 10

1-Phenyl-3,4-Dihydroxy-2(1H)-Quinolinone (Formula 1.6 from Formula 1.05)

Obtained from 1-phenyl-3-oximino-quinolin-2,4(1H)-dione (Formula 1.05, Example 4) using the hydrolytic reduction procedure described in Example 7. That the expected product was obtained was confirmed by the spectral data: MS: m/e 254 (M.+ +1).

EXAMPLE 11

1-Methyl-3,4-di(N-Methyl-Pyrrol-2-carbonyloxy)-2(1H)-Quinolinone (Formula 1.4 from Formula 1.02)

Thionyl chloride (10 ml) was added to N-methyl-pyrrole-2-carboxylic acid (2.5 gm) in ether (10 ml), the mixture was refluxed for 20 mins and evaporated under reduced pressure. The residual oil was azeotroped with benzene. The resulting acid chloride was dissolved in methylene chloride (10 ml) and added to a solution of 1-methyl-3,4-dihydroxy-2(1H)-quinolinone (1.7 gm, Example 7, obtained from Formula 1.02, see Example 1)

in pyridine (20 ml). The reaction mixture was stirred overnite at room temperature, then diluted with methylene chloride, then washed with water, then dried and then evaporated under reduced pressure. The crude product was then purified by chromatography on silica gel using chloroform as the eluting solvent. Fractions containing the major product (silica gel tlc plates; 12.5% ethyl acetate/chloroform solvent system) were combined and crystallized from ethyl acetate to give the title compound (2.24 gm). That the expected product was obtained was confirmed by the spectral data: MS (FAB): m/e 406 (M.$^+$+1); NMR(CDCl$_3$): δ3.81 (s, 3H, CH$_3$—N), 3.90 (s, 3H, CH$_3$—N), 3.92 (s, 3H, CH$_3$—N), 6.10, 6.19, 6.81, 6.89, 7.12, 7.26(m, 6H, Pyrrole) ppm.

EXAMPLE 12

1-Methyl-3,4-di-(Pyrrole-2-carbonyloxy)-2(1H)-Quinolinone (Formula 1.5 from Formula 1.02)

Obtained by acylation of 1-methyl-3,4-dihydroxy-2(1H)-quinolinone (Example 7, obtained from Formula 1.02, see Example 1) with pyrrole-2-carboxylic acid using the procedure described in Example 11. That the expected product was obtained was confirmed by the spectral data: MS: m/e 377 (M.$^+$); NMR(CDCl$_3$): δ3.79 (s, 3H, CH$_3$—N), 6.22 (m, 1H, =CH), 6.34 (m, 1H, =CH), 6.95 (m, 1H, =CH), 7.06 (m, 2H, =CH), 7.21 (m, 1H, =CH), 7.30 (m, 1H, =CH), 7.44 (d, 1H, =CH), 7.60 (m, 1H, =CH), 7.72 (d, 1H, =CH), 9.31 (br, 1H, NH), 9.49 (br, 1H, NH) ppm.

EXAMPLE 13

1-Methyl-3,4-di-(4-bromo-2-furoyloxy)-2(1H)-Quinolinone (Formula 1.7 from Formula 1.02)

Obtained by acylation of 1-methyl-3,4-dihydroxy-2(1H)-quinolinone (Example 7, obtained from Formula 1.02, see Example 1) with 2-bromo furoic acid using the procedure described in Example 11. That the expected product was obtained was confirmed by the spectral data: MS(FAB): m/e 538 (M.$^+$+1); NMR(CDCl$_3$): δ3.81 (s, 3H, CH$_3$—N), 6.50, 6.58, 7.32, 7.44 (d, 4H, Furan) ppm.

EXAMPLE 14

1-Methyl-3,4-di-(2-Thienylcarbonyloxy)-2(1H)-Quinolinone (Formula 1.8 from Formula 1.02)

Obtained by acylation of 1-methyl 3,4-dihydroxy-2(1H)-quinolinone (Example 7, obtained from Formula 1.02, see Example 1) with thiophene-2-carboxylic acid using the procedure described in Example 11. That the expected product was obtained was confirmed by the spectral data: MS(FAB): m/e 412(M.$^+$+1); NMR(CDCl$_3$): δ3.82 (s, 3H, CH$_3$—N) ppm.

EXAMPLE 15

1-Methyl-3,4-di-(iso-Nicotinyloxy)-2(1H)-Quinolinone (Formula 1.12 from Formula 1.02)

Obtained by acylation of 1-methyl-3,4-dihydroxy-2(1H)-quinolinone (Example 7, obtained from Formula 1.02, see Example 1) with isonicotinic acid using the procedure described in Example 11. That the expected product was obtained was confirmed by the spectral data: MS(CI): m/e 402 (M.$^+$+1); NMR(CDCl$_3$): δ3.87 (s, 3H, CH$_3$—N), 8.80 (d, 2H, CH=N), 8.90(d, 2H, CH=N) ppm.

EXAMPLE 16

1-Methyl-3,4-di-Benzoxy-2(1H)-Quinolinone (Formula 1.9 from Formula 1.02)

Obtained by acylation of 1-methyl-3,4-dihydroxy-2(1H)-quinolinone (Example 7, obtained from Formula 1.02, see Example 1) with benzoyl chloride using the procedure described in Example 11. That the expected product was obtained was confirmed by the spectral data: MS(FAB): m/e 400 (M.$^+$+1); NMR(DMSO): δ3.83 (s, 3H, CH$_3$—N), 8.17 (m, 4H, =CH—CO) ppm.

EXAMPLE 17

1-Methyl-3,4-di-Acetoxy-2(1H)-Quinolinone (Formula 1.13 from Formula 1.02)

Obtained by acylation of 1-methyl-3,4-dihydroxy-2(1H)-quinolinone (Example 7, obtained from Formula 1.02, see Example 1) with acetic anhydride in pyridine and purifying the product by the procedure described in Example 11. That the expected product was obtained was confirmed by the spectral data: MS(CI): m/e 276 (M.$^+$+1); NMR(DMSO): δ2.31 (s, 3H, CH$_3$COO), 2.48(s, 3H, CH$_3$COO), 3.70 (s, 3H, CH$_3$—N) ppm.

EXAMPLE 18

1-Methyl-3,4-di-Propionoxy-2(1H)-Quinolinone (Formula 1.10 from Formula 1.02)

Obtained by acylation of 1-methyl-3,4-dihydroxy-2(1H)-quinolinone (Example 7, obtained from Formula 1.02, see Example 1) with propionic anhydride in pyridine and purifying the product by the procedure described in Example 11. That the expected product was obtained was confirmed by the spectral data: MS(FAB): m/e 304 (M.$^+$+1); NMR(CDCl$_3$): δ1.30 (t, 3H, CH$_3$), 1.36 (t, 3H, CH$_3$), 2.70 (m, 4H, CH$_2$CO), 3.76(s, 3H, CH$_3$—N) ppm.

EXAMPLE 19

1-Methyl-3,4-di-Methoxy-2(1H)-Quinolinone (Formula 1.11 from Formula 1.02)

A suspension of 1-methyl-3,4-dihydroxy-2(1H)-quinolinone (0.2 gm, Example 7, obtained from Formula 1.02, see Example 1) in methylene chloride (5 ml) and methanol (5 ml) was treated with a solution of excess diazomethane in ether. The resulting solution was evaporated and the residue was chromatographed on silica gel (5 gm). The major product of the reaction was eluted with 1% methanol/methylene chloride and crystallized from ethyl acetate-hexane to give the title compound. That the expected product was obtained was confirmed by the spectral data: MS: m/e 219 (M.$^+$+1); NMR(CDCl$_3$): δ3.71 (s, 3H, CH$_3$—N), 3.94 (s, 3H, OCH$_3$), 4.22 (s, 3H, OCH$_3$) ppm.

EXAMPLE 20

3,4,7-Trihydroxy-8-methyl-1,2-benzopyrone (Formula 1.14 from Formula 1.06)

Obtained from Formula 1.06 (Example 5) using the hydrolytic reduction procedure described in Example 7.

EXAMPLE 21

3,4-Dihydroxy-1,2-benzothiopyrone (Formula 1.15 would be obtained from Formula 1.07)

The title compound would be obtained if the compound of Formula 1.07 (Example 6) were to be reductively hydrolyzed using the procedure described in Example 7.

BIOLOGICAL DATA

Cell and Virus Culture

HeLa and Vero cell cultures were maintained in Eagles Minimal Essential Medium which was supplemented with glutamine, penicillin, streptomycin and 10% fetal calf serum (10% EMEM). Stock cultures of HSV-2 (strain MS available from ATCC VR-540) were grown in and harvested from Vero cells. Viral stocks were titered in Vero cells according to established procedures.

Plasmid Constructions

Plasmid pON 245$^{ori-}$ contains the promoter of the HSV-1 thymidine kinase (tk) gene located immediately 5′ of the *E. coli* lac Z gene. In this arrangement, the tk promoter controls transcription from the bacterial gene in transient expression assays. Additionally, an SV40 polyadenylation signal is present at the 3′ end of the lac Z gene to allow for the efficient translation of the mRNA in eucaryotic cells. The expression of beta galactosidase in a transient assay using pON 245$^{ori-}$ is dependent upon superinfection of the transfected cells with HSV. Therefore, a compound which interferes with early steps of HSV replication will also inhibit beta galactosidase production in transfected cells. For example, see U.S. application Ser. No. 07/435,491 filed Sep. 5, 1989, the disclosure of which is incorporated herein by reference thereto.

Transient Expression of Beta Galactosidase in Transfected Cells

HeLa cells were seeded into 96 well microtiter plates and allowed to grow to 80% confluency (approximately 35000 cells/well). One half microgram of plasmid pON 245$^{ori-}$ DNA was introduced into the cells of each well by the DEAE Dextran precipitation technique (Grahman and Van der Eb, 1973). Four to six hours later, the cells were rinsed with Hank's Balanced Salt Solution (HBSS), overlaid with 10% EMEM and incubated at 37° C. At 24 hrs post-transfection, cells were rinsed, overlaid with 10% EMEM again and re-incubated at 37° C. At 48 hrs. post-transfection, cells were rinsed and overlaid with either EMEM containing 2% fetal calf serum (2% EMEM), 2% EMEM containing HSV-2 (strain MS, Multiplicity of Infection [moi]=5 pfu/cell) or 2% EMEM containing HSV-2 and the appropriate concentration of the compound to be tested. Twenty-four hrs later, the cells were harvested and assayed for beta galactosidase activity as described below.

Beta Galactosidase Assay

All determinations of beta galactosidase activity were performed in 96 well microtiter plates. The intracellar level of beta galactosidase activity in each well was determined from cell lysates of the monolayer cultures. Aliquots were assayed by incubation in the presence of beta galactosidase substrate, 4-methylumbelliferyl-$\beta$-D-galactoside (MUG, 125 ug/ml, Sigma), for 2 hrs. The generation of fluorescent product was quantified on a Microfluor microfluorimeter (Dynatech) after addition of 0.1M glycine, pH 10.3 (Spaete and Mocarski, 1985). The inhibitory activity of a compound was plotted versus the concentration and an IC50 value (the concentration of compound required to reduce beta glactosidase expression by 50%) was obtained for each compound tested.

Compound Toxicity Assay

Compounds which demonstrated a significant inhibitory activity in the HeLa cell beta galactosidase assay were assayed for their inhibitory effect on HeLa cell translation. HeLa cells were treated with inhibitory compound for 24 hrs, after which levels of translational activity were assayed.

For assay of translational activity, HeLa cultures were grown to 80% confluency in 96 well microtiter plates, treated with appropriate concentrations of compound in 2% EMEM during an overnight incubation at 37° C., then rinsed with HBSS and overlaid with 0.8 ml of 2% EMEM containing 8 uCi of tritiated leucine ($^3$H-LEU, 141 Cu/mMol, Amersham Corp., Arlington Heights Ill.). After a 1 hr incubation at 36.5° C., the cells were rinsed twice with phosphate buffered saline (PBS) and lysed in 400 ul/well of 1×PBS, 0.5% sodium dodecyl sulphate (SDS). After a 10 min incubation at 36.5° C., the contents of the well were transferred to a well in a Millititer HA microfiltration plate (Millipore Corp., Bedford, Mass.). The TCA insoluble proteins were precipitated onto the filter disc by a 10 min fixation with 5% TCA, followed by filtration under vacuum and three 10 minute rinse with 95% ethanol. The filters were dried at room temperature, cut from the milltitier plate and transferred to scintillation vials. TCA precipitable counts were assayed in 5 ml of Scintisol (Isolab, Akron, Ohio). The inhibitory activity of a compound was plotted versus the concentration and an IC50 value (that concentration of the compound required to decrease cellular translational activity by 50%) was derived for each compound.

Analysis of In Vivo Efficacy

The in vivo assessment of anti-HSV efficacy was determined in the prophylactic guinea pig model of HSV infection described by Stansberry et al (1982). Dosing of guinea pigs was comprised of an initial treatment with test compound given 24 hrs prior to virus infection and subsequent administration of the compound every eight hours (T.I.D.) for a total of 10 days. Test compounds were administered subcutaneously in 0.5% buffered methyl cellulose at a dose of 60 mg per kg body weight of the animal. Animals were monitored daily for the developement of genital lesions and neurological symptomology, both of which were recorded and compared to the results obtained with parallel groups which received placebo or acyclovir treatment. Efficacy was evaluated for each compound by scoring the ability of the compound to ameliorate genital lesions produced by infection with HSV-2, strain MS, expressed as Maximum Lesion scores (MLS) on a scale of 1 (least lesions) to 4 (severe lesions).

In Vitro Anti-HSV Activity

The in-vitro anti-HSV activity of compounds of this invention is set forth in Table I. More than one number for a particular entry indicates the results for additional tests.

TABLE I

| FORMULA | ANTI-HSV ACTIVITY HSV-$\beta$-GAL ASSAY IC$_{50}$ ($\mu$g/ml) | CYTOTOXICITY $^3$H-LEU ASSAY IC$_{50}$ ($\mu$g/ml) |
| --- | --- | --- |
| 1.02 | 7 | 27 |
| 1.03 | 7 | 40 |
| 1.04 | <3, 2.5 | 37 |

In-Vivo Anti-HSV Activity

The compound of Formula 1.04 was inactive when tested in-vivo using the in-vivo protocol set forth above.

The invention being thus described, it will be obvious that the same may be varied in many ways. Such variations are not to be regarded as a departure from the spirit and scope of the invention and all such modifications are intended to be included within the scope of the claims.

What is claimed is:

1. The compound of the formula

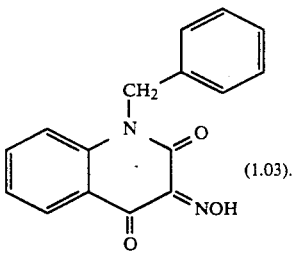

(1.03).

2. The compound of the formula

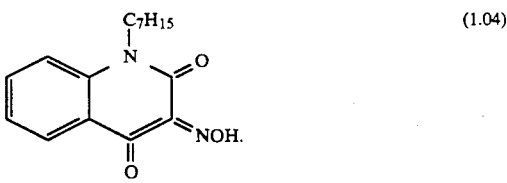

(1.04)

3. A pharmaceutical composition comprising an effective amount of a pharmaceutically acceptable carrier and an effective amount of a compound of claim 1.

4. A pharmaceutical composition comprising an effective amount of a pharmaceutically acceptable carrier and an effective amount of a compound of claim 2.

5. A method of treating a viral infection in a patient in need of such treatment comprising administering an effective amount of a compound of claim 1 to said patient.

6. A method of treating a viral infection in a patient in need of such treatment comprising administering an effective amount of a compound of claim 2 to said patient.

* * * * *